(12) United States Patent
Davey

(10) Patent No.: US 6,539,776 B2
(45) Date of Patent: Apr. 1, 2003

(54) APPARATUS FOR CONDITION MONITORING OF THE INTEGRITY OF FASTENERS AND FASTENED JOINTS

(75) Inventor: Kenneth John Davey, Bassendean, WA (US)

(73) Assignee: Structural Monitoring Systems, Ltd. (AU)

( * ) Notice: Subject to any disclaimer, the term of this patent is extended or adjusted under 35 U.S.C. 154(b) by 0 days.

(21) Appl. No.: 09/883,844

(22) Filed: Jun. 18, 2001

(65) Prior Publication Data

US 2002/0047717 A1 Apr. 25, 2002

(30) Foreign Application Priority Data

Jun. 19, 2000 (AU) .............................................. PQ8235

(51) Int. Cl.⁷ .............................. G01M 3/02; G01M 3/04
(52) U.S. Cl. ................................................ 73/37; 73/40
(58) Field of Search ................................. 73/37, 38, 40

(56) References Cited

U.S. PATENT DOCUMENTS

| | | |
|---|---|---|
| 3,918,291 A | 11/1975 | Pauly et al. |
| 4,104,906 A | 8/1978 | Oertle |
| 4,145,915 A | 3/1979 | Oertle |
| 4,651,557 A | 3/1987 | Cholet |
| 4,776,206 A | 10/1988 | Armstrong et al. |
| 4,979,390 A * | 12/1990 | Schupack et al. .......... 73/38 |
| 5,078,005 A | 1/1992 | Krempel et al. |
| 5,404,747 A | 4/1995 | Johnston et al. |
| 5,544,520 A | 8/1996 | Graf et al. |
| 5,596,137 A | 1/1997 | Perry et al. |
| 5,770,794 A * | 6/1998 | Davey .......................... 73/37 |
| 6,223,587 B1 | 5/2001 | Chiocca |

FOREIGN PATENT DOCUMENTS

| | | |
|---|---|---|
| EP | 0 177 433 | 8/1985 |
| WO | 94/27130 | 11/1994 |

\* cited by examiner

Primary Examiner—Herzon Williams
Assistant Examiner—J L P
(74) Attorney, Agent, or Firm—Allen, Dyer, Doppelt, Milbrath & Gilchrist, P.A.

(57) ABSTRACT

Apparatus 10 for condition monitoring the integrity of a rivet 12 joint holding together sheets 14 and 16 of a structure 18 includes a substantially fluid impervious pad 20 for covering the heads of the rivets 12 and an adjacent surface 24 of the structure 18. The pad 20 has a first surface 26 for placement over the rivets 12 and the surface 24. An inner portion of the surface 26 is formed or otherwise configured to define a fluid flow region 28 between the pad 20 and the rivets 12/surface 24 across which fluid can flow. The region 28 is coupled to a constant vacuum source 30 via a conduit 32 and a series coupled high fluid flow impedance 34. A transducer 38 and display 44 coupled in parallel across the impedance 34 provides an indication of change in differential pressure across the high impedance which in turn provides an indication of the presence or development of a flaw in the rivets joint.

15 Claims, 3 Drawing Sheets

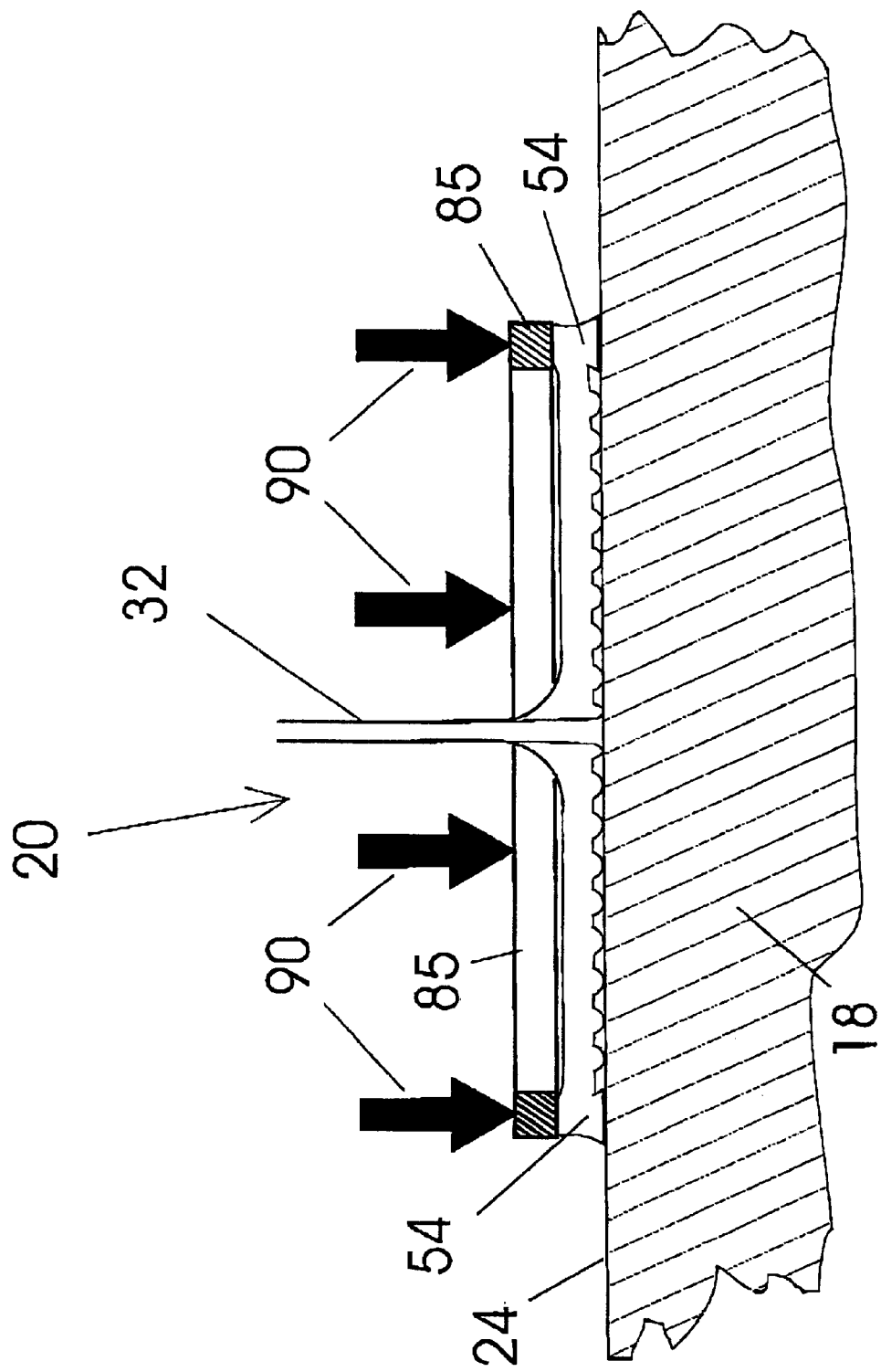

APPARATUS FOR CONDITION MONITORING OF THE INTEGRITY OF FASTENERS AND FASTENED JOINTS

FIELD OF THE INVENTION

The present invention relates to an apparatus for the condition monitoring the integrity of fasteners and fastened joints.

BACKGROUND OF THE INVENTION

One of the problems faced by aircraft designers relates to the loosening of fasteners such as rivets and bolts used on aircraft structures leading to fretting as a result of movement of the fastener or the initiation of cracking and over stressing of adjacent fasteners. Cracks or corrosion formed under fastener heads or in layers of sheet material below a surface layer can also cause fasteners to become loose.

Cracks in fasteners of pressure hulls or fuel containment areas are of great concern due to the possibility of rapid growth and catastrophic structural failure.

The present practice is to merely detect the loosening or misalignment of a fastener by detecting leaks around the fastener utilizing vacuum techniques. This method can be applied to every fastener or to selected fasteners. However, the above method does not allow quick comparative measurement.

Schupack et al U.S. Pat. No. 4,979,390 discloses a method and apparatus for testing the relative permeability of materials, and thus could be used for condition monitoring of the integrity of fasteners and fastened joints. However the method does not allow quick comparative measurement as it is not a rate measurement (ie, it is dependent on elapsed time) and further, would be structurally damaging to sheet metal structures due to localised high differential pressure forces across the test area.

SUMMARY OF THE INVENTION

It is an object of the present invention to provide an apparatus for the condition monitoring of the integrity of fasteners and fastened joints which attempts to alleviate the disadvantages of the above described prior art techniques.

According to the present invention there is provided an apparatus for the condition monitoring of the integrity of fasteners and fastened joints in a structure including at least:

a substantially fluid impervious pad for placement over a head of one or more fasteners adjacent a surface of the structure, said pad having a first surface for contacting said structure, a portion of said first surface configured to define a region facilitating a free flow of fluid across said first surface between said pad and said structure when said first surface is in contact with said structure covering said one or more fasteners;

a substantially constant vacuum source;

a high fluid flow impedance coupled between said constant vacuum source and said region; and, means for measuring differential pressure across said high fluid flow impedance.

Preferably, said pad is collapsible to the extent that said first surface can substantially conform to the contour of the head of said fasteners when said pad is in contact with said structure and the region is in fluid communication with said constant vacuum source.

Preferably, said apparatus further includes a bypass conduit connected in parallel across said high impedance between said region and said constant vacuum source, and first valve for selectively opening and closing fluid communication through said bypass conduit.

Preferably, said apparatus further includes a second valve for selectively opening and closing fluid communication through said high fluid flow impedance.

Preferably, said first surface is formed with a plurality of protrusions for contacting said fasteners and/or structure, said protrusions shaped so that gaps exist between mutually adjacent protrusions, whereby said region is in the form of a cavity defined by said gaps.

Preferably, said apparatus includes sealing means for providing a fluid tight seal about a periphery of said portion of said first surface.

Preferably, said sealing means includes an elastomeric strip provided in said pad about the periphery of said portion of said first surface.

Preferably, said sealing means further includes a channel formed in said elastomeric strip; and, said apparatus further includes means for selectively placing said channel in fluid communication with an independent vacuum source.

In an alternative embodiment, said sealing means includes means for releasably mechanically holding said elastomeric strip in sealing engagement with the surface of said structure.

BRIEF DESCRIPTION OF THE DRAWINGS

An embodiment of the present invention will now be described by way of example only with reference to the accompanying drawings in which.

DETAILED DESCRIPTION OF THE PREFERRED EMBODIMENTS

The embodiments of the present invention are described below with reference to rivet fastened joints to establish their integrity by measuring their relative permeability. However it is to be understood that the present apparatus can be used for other types of mechanical fastening including for example bolts.

Figure 1:
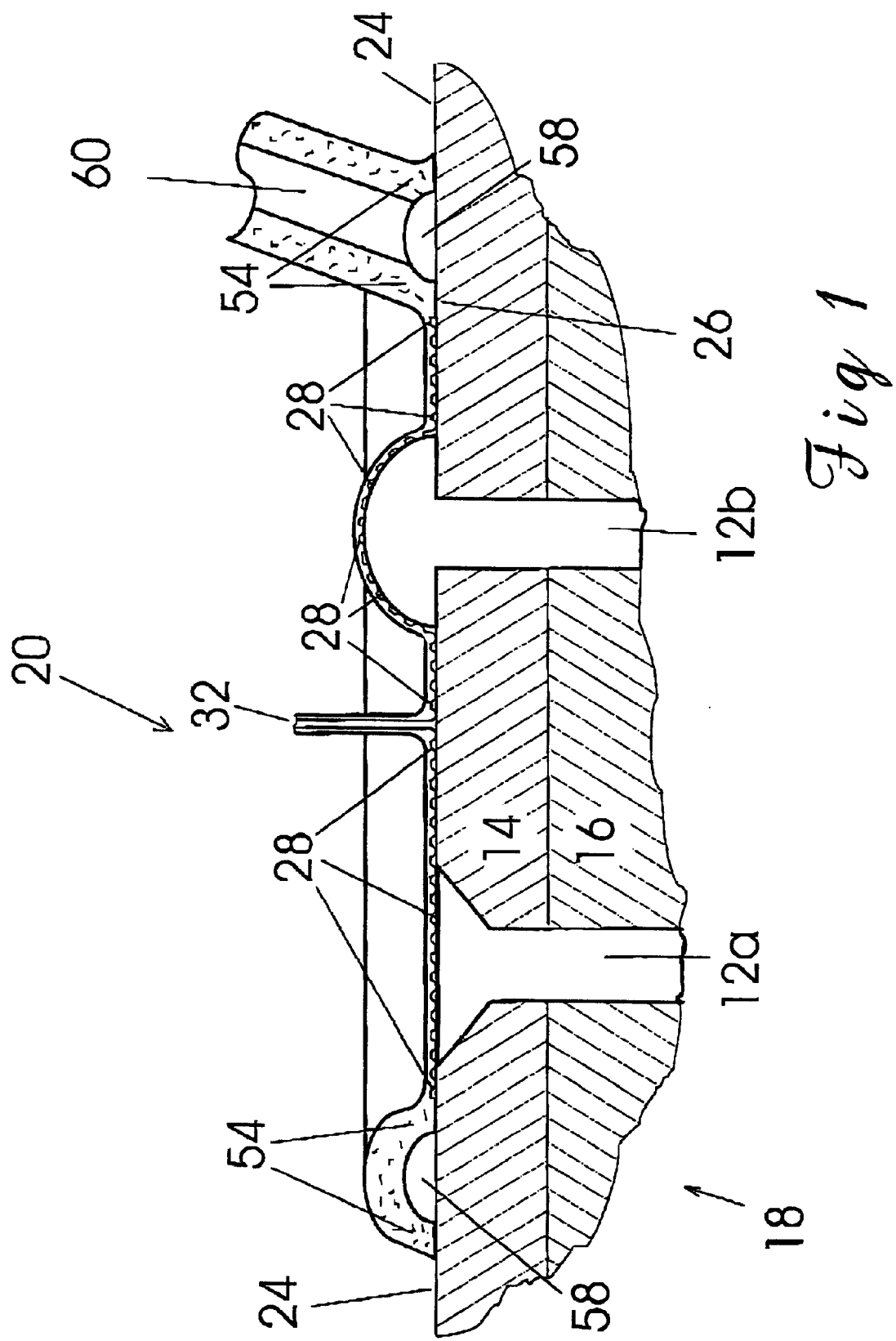
FIG. 1 is a schematic representation of the application of an embodiment of the apparatus for condition monitoring the integrity of fasteners and fastened joints in a structure.
Figure 2:
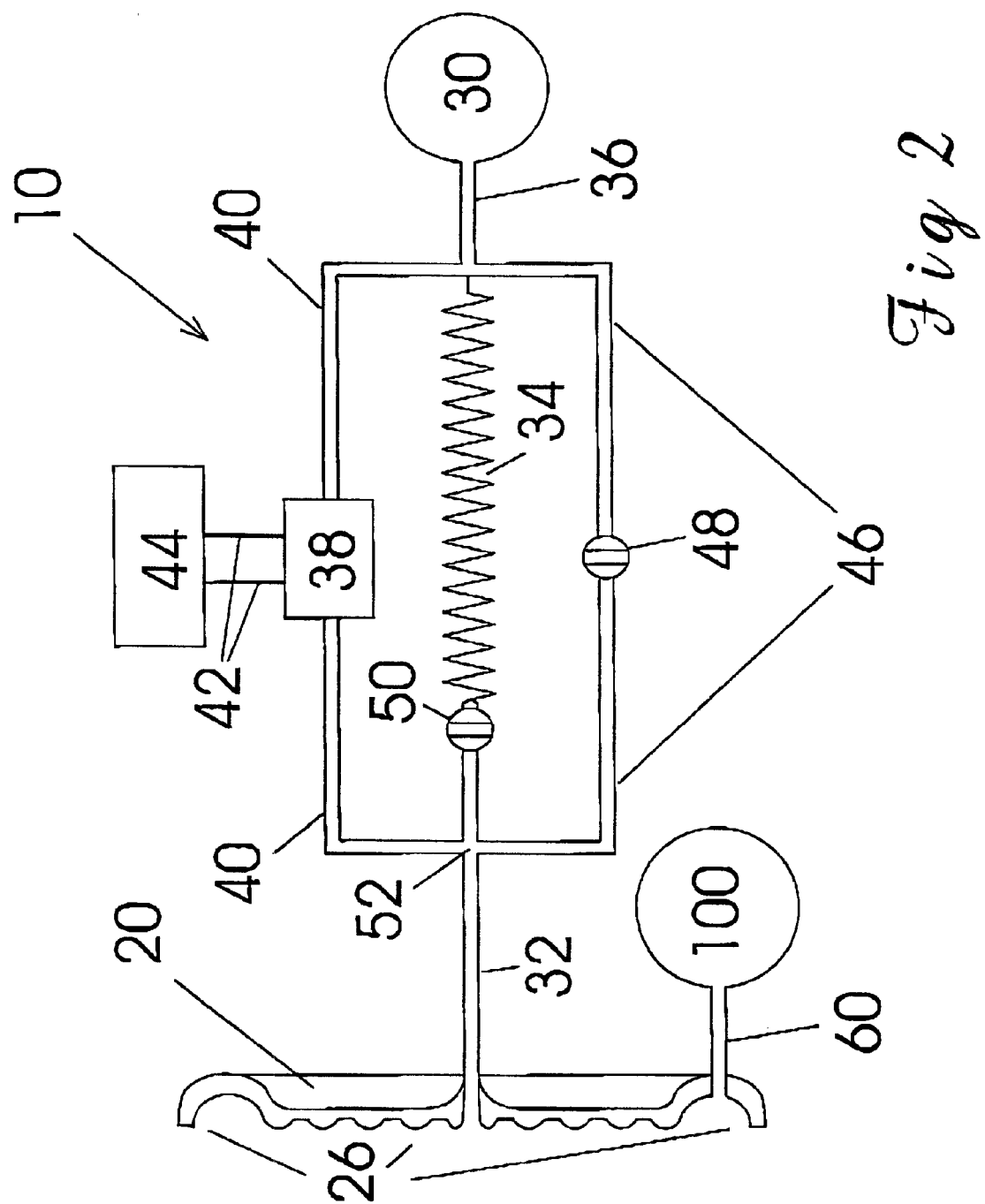
FIG. 2 is a schematic representation of an embodiment of the apparatus for condition monitoring the integrity of fasteners and fastened joints in a structure; and, FIG. 3 is a schematic representation of a pad incorporated in a second embodiment of the apparatus.

Referring in particular to FIGS. 1 and 2, the apparatus 10 for the condition monitoring the integrity of fastened joints in the form of a flush head rivet 12a and a round head rivet 12b (hereinafter referred to in general as "rivets 12") holding together sheets 14 and 16 of a structure 18 includes a substantially fluid impervious pad 20 for covering heads of rivets 12a and 12b respectively adjacent surface 24 of the structure 18. The pad 20 has a first surface 26 for placement over the rivets 12a, 12b and the surface 24 of structure 18. An inner portion of the first surface 26 is formed or otherwise configured to define a fluid flow region 28 between the pad 20 and the rivets 12/surface 24 across which fluid can flow. In this way the portion of the first surface 26 can be described as being fluid conductive. The region 28 is coupled to a constant vacuum source 30 via a conduit 32 which extends from the pad 20, valve 50, a high fluid flow impedance 34, and a conduit 36. The high fluid flow impedance 34 preferably comprises a very long length of small bore duct which allows a minuscule flow of fluid.

Alternatively, the high fluid flow impedance 34 could comprise a permeable material such as sintered glass. The magnitude of the high fluid flow impedance should be sufficiently high as to produce significant pressure drop across the high impedance in response to minuscule flow through the high impedance. Measuring means in the form of a differential pressure transducer 38 is provided in a conduit 40 which is connected in parallel across the high impedance 34 to measure differential pressure across the high impedance 34. Coupled to transducer 38 via electrical wires 42 is a display 44 to provide a visual indication of the differential pressure.

When the apparatus 10 is in use with the pad 20 placed over one or more rivets 12 after a short period of time a steady state vacuum condition will exist in the fluid flow region 28. There will also be a difference in the vacuum condition in the region 28 and the vacuum source 30 by reason of some permeable fluid flow through the intervening high impedance 34. Thus after an initial period the transducer 38 and display 44 will co-operate to provide an indication of the steady state differential pressure across the high impedance 34. In the event that a crack or corrosion were to develop in one of the rivets 12 or in the sheets 14 or 16 through which a rivet passes under the pad 20, there will be a change in vacuum condition in the region 28 leading to a change in the differential pressure which will be detected by the transducer 38 and indicated on the display 44. Similarly, if a higher than expected reading of differential pressure is measured when first applying the apparatus 10 to the surface then the integrity of fastened joints is in question.

In order to allow rapid spot checking of fasteners and fastened joints with the use of the apparatus 10, the apparatus 10 is also provided with a bypass duct 46 that extends in parallel across the high impedance 34 between the pad 20 and the vacuum source 30. A first valve 48 is provided in the conduit 46 for selectively opening and closing fluid communication through the bypass conduit 46. In addition, second valve 50 is provided in series with the high impedance 34 prior to junction 52 where the conduits 32, 46 and 40 meet to prevent vacuum loss when pad 20 is not attached to the surface of structure 24.

The purpose of the bypass conduit 46, and valve 48 is to allow for rapid stabilisation of the pressure differential across the high impedance 34 when initially applying the pad 20 to the surface 24 of structure 18. After the peripheral sealing of pad 20 to the surface 24 of structure 18 the valve 48 is opened so that the region 28 is placed in unimpeded fluid communication with the vacuum source 30 leading to a rapid evacuation of the region 28. Thereafter, the valve 48 can be closed and the second valve 50 opened so that fluid communication between the region 28 and vacuum source 30 is now via the high impedance 34.

The apparatus 10 is also provided with sealing means to provide a fluid tight seal about the periphery of region 28. In the embodiment shown in FIGS. 1 and 2 the sealing means includes an elastomeric strip 54 formed as part of the pad 20 which defines the outer limits or perimeter of the region 28. A cavity 58 is formed along the strip 54. When the pad 20 is placed on the structure 18, first surface 26 down, and the cavity 58 is placed in fluid communication with independent vacuum source 100 via a conduit 60, a seal is formed about the periphery of the region 28 so that there is no vacuum leak from between the periphery of the region 28 and the surface 24 of structure 18.

In the present embodiment, the elastomeric strip 54 and the surface 26 of the pad 20 are made from one and the same material however the thickness and surface finish of the material for the elastomeric strip 54 and the sheet 26 are varied in accordance with their different function. In particular, the material forming the portion of the pad 20 constituting the surface 26 has a degree of collapsibility sufficient so that the surface 26 can substantially conform to the contour of the rivets 12 and in general, to the contour of surface 24 when the pad 20 is placed on the structure 18 and the region 28 is in fluid communication with the constant evacuative source. This self contouring effect of pad 20 is clearly depicted in FIG. 1.

However, the pad 20 need not be made from a single piece of the same material. For example, the pad 20 can be made by attaching the elastomeric strip 54 about a piece or sheet of collapsible or compliant material, which bears the surface 26. For example, the pad 20 can be formed from a sheet of polyethylene coated silk having an attached rubber, or other elastomeric material, perimeter strip. The perimeter strip allows the pad 20 to be sealed to the structure 18 while the surface of the polyethylene coated silk adjacent the structure 18 forms the surface 26 which, in turn, defines the fluid flow region 28.

As previously described, the surface 26 is formed or otherwise configured to allow a free flow of fluid across the surface 26 in the region 28. In this way, the surface 26 can be said to be fluid conductive. One way of achieving this is to form a plurality of small protrusions such as dimples on the surface 26 which is shaped or otherwise configured so that a gap exists between mutually adjacent dimples. Thus, when the first surface 26 is placed into contact with the structure 18, a matrix or network of gaps exist between the dimples to allow a free flow of fluid across the surface 26. The matrix or network of gaps in effect, creates a cavity or what could be viewed as a plurality of cavities in fluid communication with each other.

Another way of achieving this effect is to form the first surface 26 as a layer of a permeable material with a non-permeable coating. In a further variation particles can be embedded or adhered to the surface 26 in a random manner, somewhat akin to the formation of sandpaper to roughen the surface 26 so that the region 28 is comprised of a matrix of gaps between the particles.

In one practical realisation of the embodiment of FIGS. 1 and 2, the vacuum pressure of source 30 is 20 kPa below atmospheric reference; the impedance 34 is in the form of a plastic tube about 3 metres long with a less than 0.3 mm diameter; the transducer 38 is a common pressure transducer and amplifier and the pad 20 is made from composite silicone rubber and rubber coated cloth and defines a minimum volume for the test area when coupled to the vacuum source 30.

FIG. 3 depicts an alternate form of sealing means for the pad 20. In the embodiment shown in FIGS. 1 and 2, the sealing of the pad 20 on to the surface 24 of structure 18 is achieved by forming a cavity 58 in the perimeter strip 54 and evacuating the cavity 58 by fluid connection with the independent vacuum 100. However in FIG. 3, the sealing is achieved by mechanically holding the perimeter strip 54 on to the surface 24. In this embodiment this is achieved by placing a peripheral ring 85 on the pad 20 over lying the peripheral strip 54 and then applying a force 90 onto the ring 85. The force 90 can be applied by any appropriate mechanical means such as a clamp. Magnetic means can also be used to apply the force 90. In the case where the structure 18 is made from a magnetisable material the magnetic force 90 can be provided by forming the ring 85 from a magnetic material.

All modifications and variations as would be apparent to those of ordinary skill in the art are deemed to be within the scope of the present invention the nature of which is to be determined from the above description and the appended claims.

The claims defining the invention are as follows:

1. An apparatus for the condition monitoring of the integrity of fasteners and fastened joints in a structure including at least:

a substantially fluid impervious pad configured to overlie a head of one or more fasteners adjacent a surface of the structure, said pad having a first surface for contacting said structure, a portion of said first surface configured to define a region facilitating a free flow of fluid across said first surface between said pad and said structure when said first surface is in contact with said structure overlying said one or more fasteners;

a substantially constant vacuum source;

said pad being collapsible to the extent that said first surface substantially conforms to the contour of the head of said fasteners when said pad is in contact with said structure and the region is in fluid communication with said constant vacuum source;

a high fluid flow impedance coupled between said constant vacuum source and said region; and, a measuring device for measuring differential pressure across said high fluid flow impedance.

2. An apparatus according to claim 1 further including a bypass conduit connected in parallel across said high impedance between said region and said constant vacuum source, and first valve for selectively opening and closing fluid communication through said bypass conduit.

3. An apparatus according to claim 2 further including a second valve for selectively opening and closing fluid communication through said high fluid flow impedance.

4. An apparatus according to claim 1 wherein said first surface is formed with a plurality of protrusions for contacting said fasteners and/or structure, said protrusions shaped so that gaps exist between mutually adjacent protrusions, whereby said region is in the form of a cavity defined by said gaps.

5. An apparatus according to claim 1 further including a seal for providing a fluid tight seal about a periphery of said portion of said first surface.

6. An apparatus according to claim 5 wherein said seal includes an elastomeric strip provided in said pad about the periphery of said portion of said first surface.

7. An apparatus according to claim 6 wherein said seal further includes a channel formed in said elastomeric strip; and, said apparatus further includes an independent vacuum source in fluid communication with said channel.

8. An apparatus according to claim 6 wherein said seal includes a device for releasably mechanically holding said elastomeric strip in sealing engagement with said structure.

9. An apparatus for the condition monitoring of the integrity of fasteners and fastened joints in a structure including at least:

a substantially fluid impervious pad configured to overlie one or more fasteners extending through said structure, said pad having a first surface for contacting said structure, said first surface provided with a plurality of projections depending therefrom for contacting said structure to create a fluid flow region across said first surface between said pad and said structure, and a fluid tight seal about a periphery of said first surface, said pad being collapsible to substantially conform to the shape of said one or more fasteners and the structure overlaid by said pad.

10. The apparatus according to claim 9 wherein said seal includes an elastomeric strip provided in said pad about said first surface.

11. The apparatus according to claim 10 wherein said seal includes a channel formed in said elastomeric strip, and said apparatus further includes an independent vacuum source in fluid communication with said channel.

12. The apparatus according to claim 10 wherein said seal includes a device for releasably mechanically holding said elastomeric strip in sealing engagement with said structure.

13. The apparatus according to claim 9 further including a substantially constant vacuum source; a high fluid flow impedance between said constant vacuum source and said region; and, a measuring device for measuring differential pressure across said high fluid flow impedance.

14. The apparatus according to claim 13 including a bypass conduit connected in parallel across said high impedance between said region and said constant vacuum source, and a first valve for selectively opening and closing fluid communication through said bypass conduit.

15. The apparatus according to claim 14 including a second valve for selectively opening and closing fluid communication through said high fluid flow impedance.

* * * * *